(12) United States Patent
Dussault

(10) Patent No.: US 7,481,833 B2
(45) Date of Patent: Jan. 27, 2009

(54) THERAPEUTIC CHEST

(75) Inventor: Michel Dussault, 3632 Caryas Avenue, Charlesbourg, Quebec (CA) G1G 3E7

(73) Assignee: Michel Dussault, St-Georges (CA)

( * ) Notice: Subject to any disclaimer, the term of this patent is extended or adjusted under 35 U.S.C. 154(b) by 445 days.

(21) Appl. No.: 11/012,305

(22) Filed: Dec. 16, 2004

(65) Prior Publication Data
US 2006/0136020 A1   Jun. 22, 2006

(30) Foreign Application Priority Data
Dec. 23, 2003   (CA)   ..................................... 2450633

(51) Int. Cl.
*A61N 5/04* (2006.01)
(52) U.S. Cl. .............................. 607/91; 607/96; 607/108
(58) Field of Classification Search .................... 607/81, 607/90, 91, 96, 98, 108
See application file for complete search history.

(56) References Cited

U.S. PATENT DOCUMENTS

| | | | | |
|---|---|---|---|---|
| 811,094 | A * | 1/1906 | Robertson .................... 607/115 |
| 1,968,015 | A * | 7/1934 | Cooke et al. ................... 607/81 |
| 2,184,418 | A * | 12/1939 | Faigle ............................ 607/81 |
| 4,309,999 | A * | 1/1982 | Lueder .......................... 607/81 |
| 4,501,275 | A * | 2/1985 | Maahs ........................... 607/81 |
| 4,671,284 | A * | 6/1987 | Wilson et al. ................... 607/81 |
| 4,825,868 | A * | 5/1989 | Susa et al. .................... 607/100 |
| 5,279,290 | A * | 1/1994 | Hansen ........................ 607/98 |
| 6,004,344 | A * | 12/1999 | Fujii ............................ 607/91 |
| 6,549,809 | B2 * | 4/2003 | Ono ............................ 607/100 |
| 6,613,071 | B1 * | 9/2003 | Fujii ............................ 607/91 |
| 2004/0260364 | A1 * | 12/2004 | Daffer et al. .................. 607/81 |

* cited by examiner

*Primary Examiner*—Roy D Gibson
(74) *Attorney, Agent, or Firm*—Goudreau Gage Dubuc

(57) ABSTRACT

A therapeutic apparatus, comprising a base and a container supported by the base, the container being hollow, elongate, with angles comprised between 30 and 60 degrees, the container comprising a front part that slides relative to a rear part on rails, the container being made of stainless steel and wood; in which a user lies to be submitted to heat diffused by radiant strips, the head of the user remaining out of the container and isolated from the rest of the body by a removable flap mounted on the front part of the container.

15 Claims, 5 Drawing Sheets

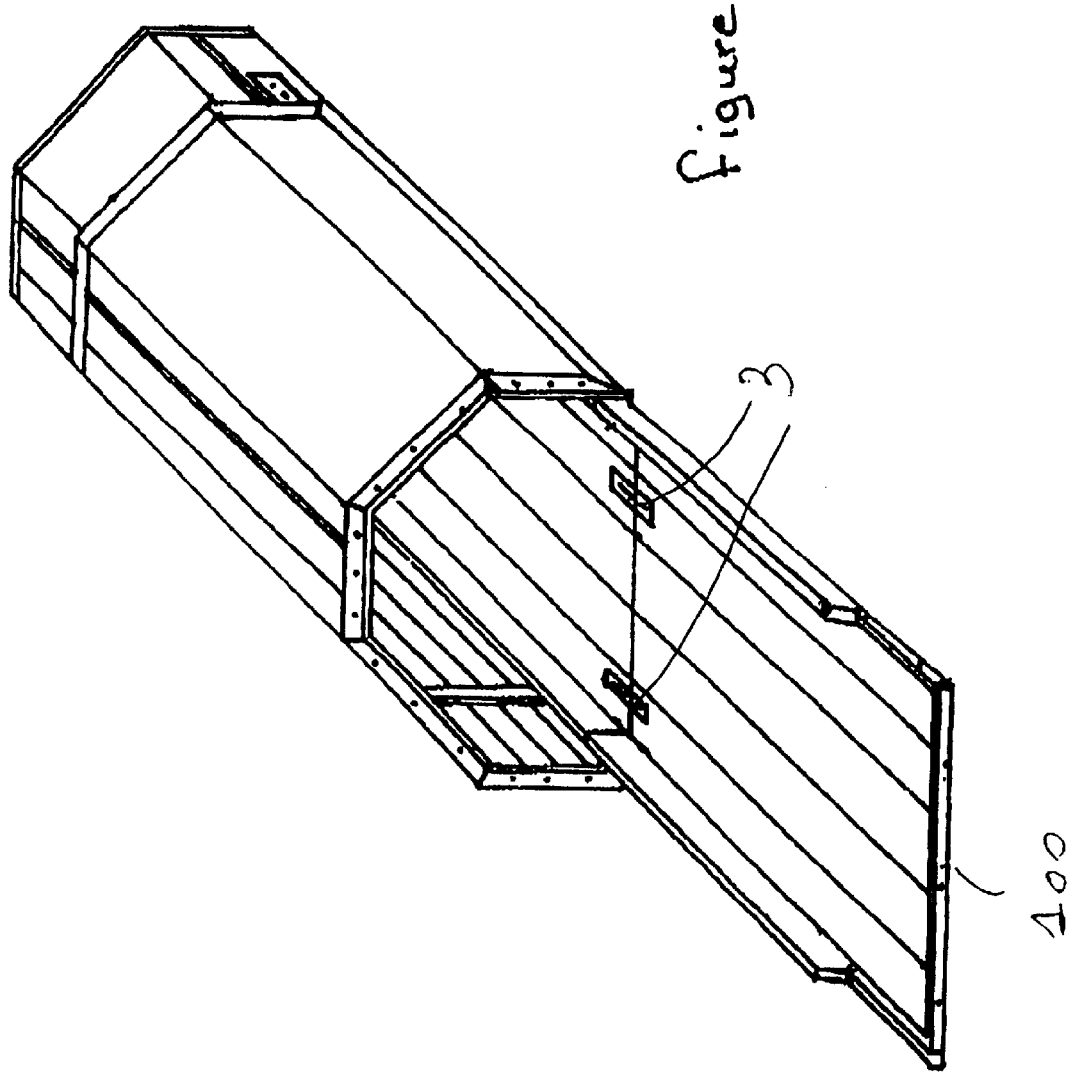

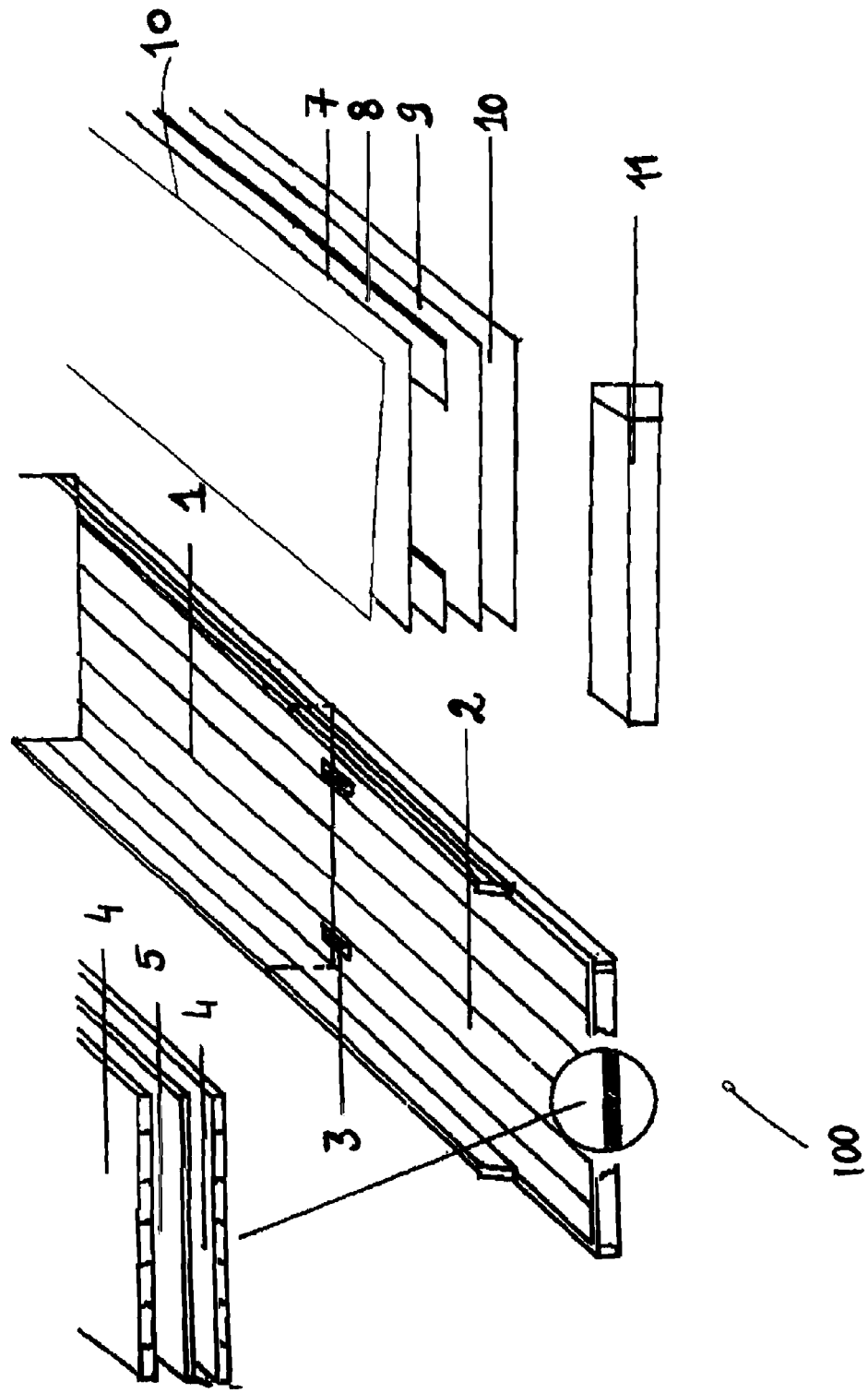

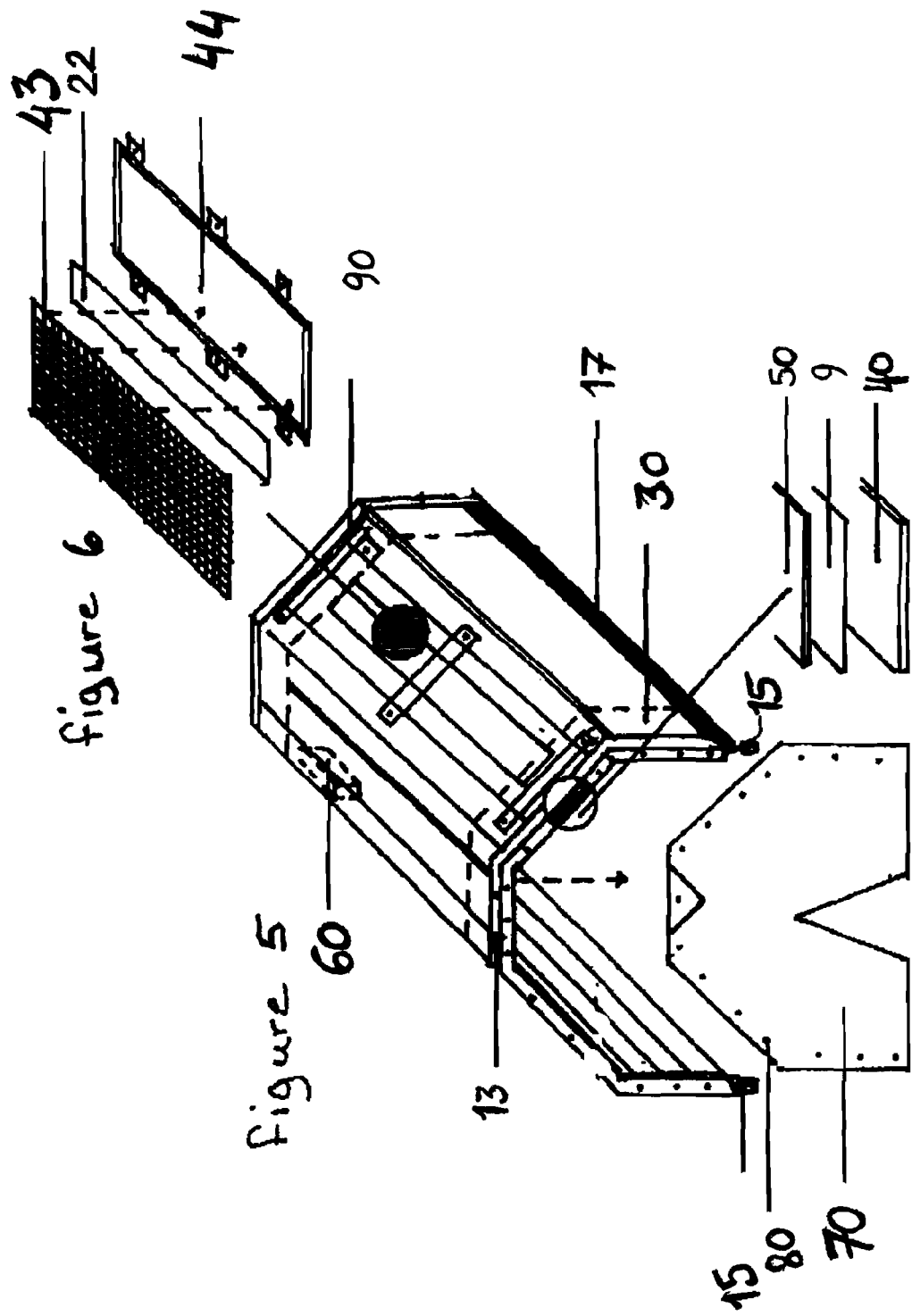

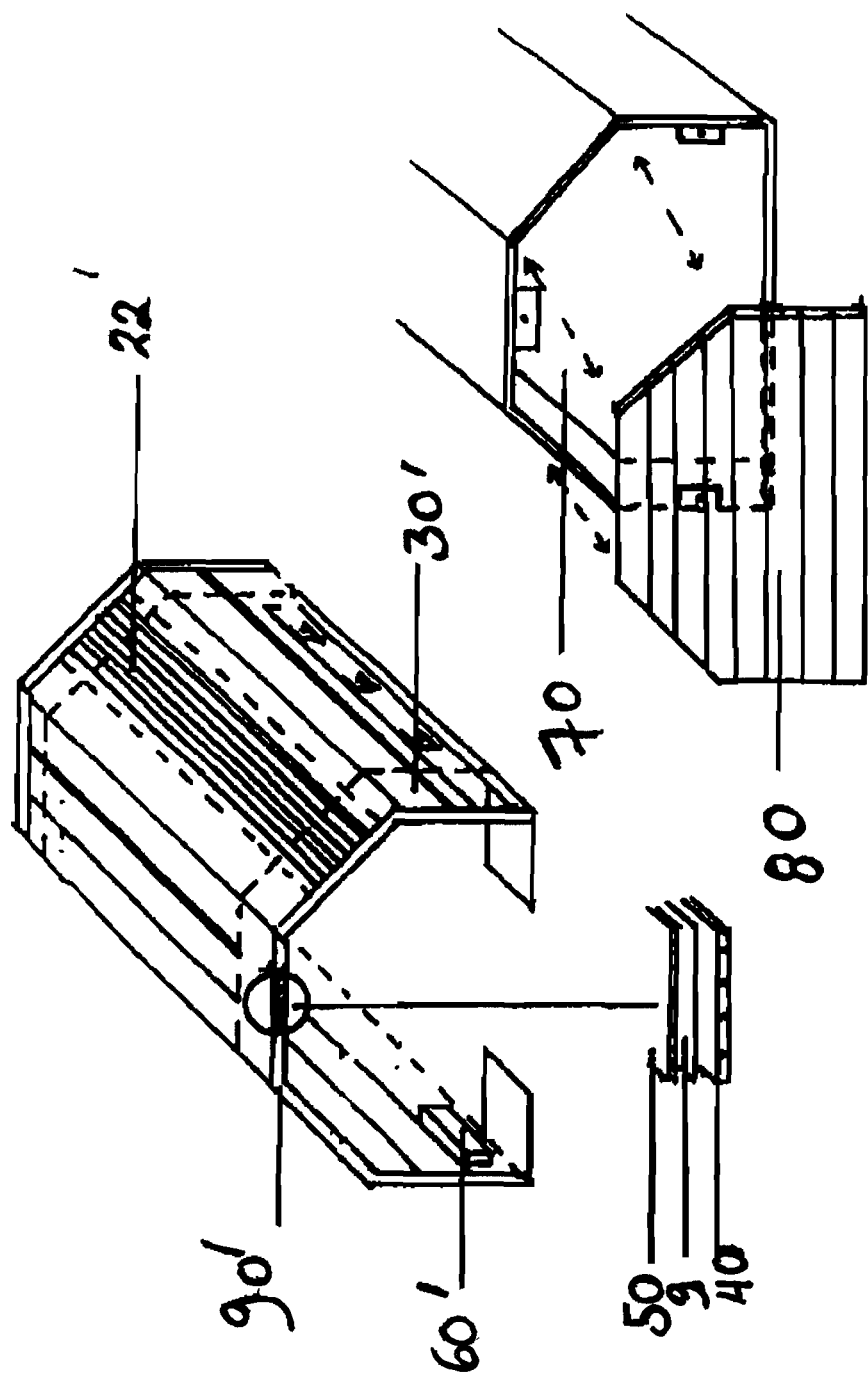

THERAPEUTIC CHEST

FIELD OF THE INVENTION

The present invention relates to a therapeutic chest, for use by a user to stretch into in order to alleviate muscular pains whilst controlling his/her weight. The chest uses dry heat and infrared distributed by radiating strips.

BACKGROUND OF THE INVENTION

Certain types of sauna or therapeutic chests have been created in the past. Most use only heat to obtain therapeutical benefits. These saunas permit the users to loose accumulated water and obtain some skin benefits. Few saunas use infrared. Actually, only one sauna uses infrared and dry heat to permit weight control without any other therapeutic advantages. The current dry heat and infrared sauna has a number of drawbacks. Being made of plastic, it tends to eventually crack, the heating elements are inadequately spread, the infrared is not sufficient and inadequately spread, the heating elements of tubular design does not distribute the heat properly, the electronic system is deficient, obese users are regularly burnt by the heat and absence of any king of security system. In addition, many different beneficiaries cannot use these apparatus.

There is therefore a need in the art for a therapeutic chest.

SUMMARY OF THE INVENTION

More specifically, in accordance with the present invention, there is provided a therapeutic apparatus, comprising a base and a container or chest having a cover supported by said base, the container being hollow, elongate, with angles comprised between 30 and 60 degrees, the container comprising a front part that slides relative to a back part on rails, the container being made of stainless steel and wood, in which a user lies to be submitted to heat diffused by radiant strips, the head of the user remaining out of the container and isolated from the rest of the body by a removable flap mounted on the front part of the container.

Other objects, advantages and features of the present invention will become more apparent upon reading of the following non-restrictive description of specific embodiments thereof, given by way of example only with reference to the accompanying drawings.

BRIEF DESCRIPTION OF THE DRAWINGS

In the appended drawings:

FIG. 2 is a view of the chest of FIG. 1, in an opened position;

FIG. 3 shows a front and a cross-sectional view of a basis for a chest according to an embodiment of the present invention;

FIG. 4 shows a mattress as used in a chest according to an embodiment of the present invention;

FIG. 5 is a detailed front view of a chest according to an embodiment of the present invention;

FIG. 6 shows radiant bands as used in a chest according to an embodiment of the present invention; and FIG. 7 is a detailed back view of a chest according to an embodiment of the present invention.

DESCRIPTION OF ILLUSTRATIVE EMBODIMENTS

Figure 1:
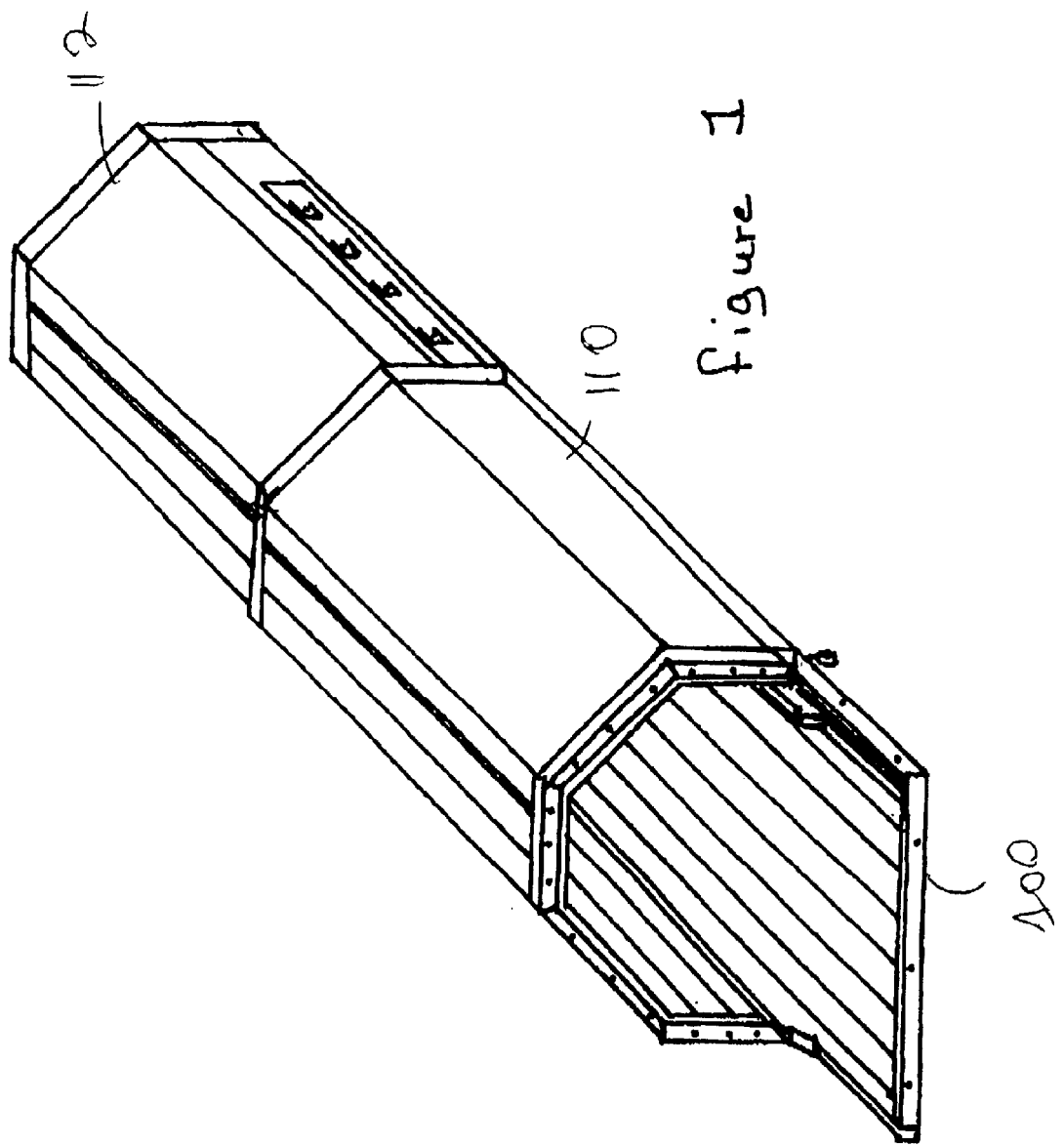
FIG. 1 is a view of a chest according to an embodiment of the present invention, in a closed position.

There is provided a chest, easy to open, which can be used even by persons of limited mobility. The structure and form of the chest is very different from other saunas already on the market. It is designed with angles permitting a controlled spreading of dry heat and infrared for treatment of most hidden parts of the body. In addition, the chest comprises an air chamber by which it rapidly reaches the desired degree of heat and it efficiently retains that heat. The chest may be adaptable to treat only the lower parts of the body. This is made possible by a flap and the opening system not found in any other sauna. The present chest is equipped with a radiating mattress and an electromagnetic security system, which stops the device immediately upon opening of the chest for the security of the user. The use of well-distributed infrared allows users to obtain numerous therapeutic benefits, such as alleviation of arthritic pains, arthritis, rheumatism or other muscular pain whilst always helping in weight-control efforts.

There is provided a hollow long-limbed compartment, structured with 45 and 90-degree angles. A user lies down therein to receive a treatment. His head remains outside the chest.

The chest if built of stainless and cedar wood.

It comprises four distinctive parts: a back part; a front part, a base and a mattress.

As shown in FIG. 3, the base (100) consists of two parts, a front base (2) and a rear base (1) fastened together by two hinges (3). To insure the solidity of the assembly, both parts are made of two slabs of cedar wood (4) and a layer of plywood (5) is included between these two slabs. The base (100) supports a mattress, so as to provide a comfortable treatment for the back.

As shown in FIG. 4, the mattress includes radiating strips (8). The mattress is made of several different materials: the exterior is made of leather (10), the interior is made of radiating strips diffusing infrared (8), radiating felt (9) and ordinary felt (7). These felts allow a uniform diffusion of the radiants and the conservation of heat. The unique conception allows a uniform treatment of the back of the user in comfort and security. The mattress completely covers the base (100) of the chest to help protect the cedar wood and facilitate the cleaning of the apparatus. For comfort, a head-rest (11) is added to the mattress.

The front part of the chest having a cover (110), illustrated in FIG. 5, is made of brushed stainless and cedar wood. The exterior (50) of the chest is made of brushed stainless to obtain a strong resistance and solidity of the chest. The interior (40) is made of cedar wood so that essential oils may be used without deteriorating the wood. The beauty of these components represents an asset for the user. An air chamber is provided between these two materials, as an air-free space between the stainless and the wood, where the heat is stored, as well as the radiating felt (9) for maintaining the heat uniform, and aluminum braces (30) that strengthen the assembly and constitute its frame. Wooden mouldings (90) are provided to accentuate the beauty of the chest. The front chest further comprises an operating indicator light (13), fasteners (80) for a bib type flap which goes around the neck of the user, the bib type flap itself (70) being secure and agreeable to the touch. It provides an air tightness of the chest and adaptation for the treatment of the torso and superior members of the body of the user.

To facilitate an effortless opening of the chest, the front part is provided with sliding rails (17) and rollers (15), allowing the user to slowly slide the front chest (110) in the rear chest (112). This allows all users, even those of limited mobility, to use this apparatus.

Two radiating strips (22) made to measure are further installed at an angle. These strips diffuse infrared and radiants. A case (60), which is airtight, is provided to protect the wiring and an electromagnetic security system. Premature aging of the chest is monitored by the security system, which also sees to the security of the user. The security system automatically stops the apparatus when the front part (110) is pulled back.

The rear part of the chest, as shown in FIG. 7, is conceived and built with materials identical to the front part. To open the chest, the front part slides over the rear part. The rear chest is also provided with two radiating strips (22'), sliding rails, aluminum braces (30'), wiring installed in an airtight aluminum case (60') and wooden mouldings (90'). The rear part includes a specific compartment for the electronic system, which ensures control of the apparatus as a control panel (70). This panel (70) is manipulated by the users to set the duration of the treatment and the desired degree of heat. A cedar wood panel (80) closes the rear end of the chest.

The radiants, shown in FIG. 6, are heating, radiating elements, which diffuse infrareds, made of heating wires integrated between rubber strips.

The body of the user is submitted to the action of ionizing radiation, which travels, by rays going in all directions. The spreading of the rays on the body causes a reaction of the organism, which, in turn, emits heat. The heat being accentuated by the radiants, the body toxins are removed thus permitting a weight control and an improved condition of the body. Muscular pains are alleviated by the rays and the heat. The cardio-vascular rhythm is increased.

The radiating elements have a unique disposition. The radiating strips (22) and a rubberized silicone covered metal grill (43) are not in contact with the apparatus nor the user, but fastened or retained by plastic rings in a hollow part of the top of the chest to insure the security of the users and the apparatus resistance. A stainless plate (44) is inserted between the apparatus and the radiants. The grill (43) is heat resistant without being a heat conductor so that it can uniformly distribute the rays and the heat whilst protecting the users.

The present chest is very different from other saunas on the market, due to its use of radiant and dry heat spread evenly through the whole chest. In addition, the user's back is relieved by the radiating mattress. Such a mattress is non-existent in all other types of saunas.

The present assembly may accommodate all persons, even those of limited mobility.

The user programs the time and the degree of heat desired on the control panel, and opens the chest to slide and stretch inside, the chest being in its open position (See FIG. 2).

When the user lies on the base (100), he slides the front chest (110) over his torso, so that only his/her head remains visible (see closed position FIG. 1). To cover his/her neck, the user may install the bib type flap around his/her chest. The treatment may last up to 35 minutes. The heat can reach 150 degrees Fahrenheit.

The base is made of cedar wood. The base closes the chest at the bottom end in order to maintain a desired heat.

For comfort and back treatment, a radiating mattress is installed on the base (see FIG. 4).

The front chest (110) slides to permit the opening and closing of the chest. A removable bib type flap provides air tightness of the chest and allows adapted treatments.

The radiant strips (FIG. 6) diffuse infrared for the treatment of the users. Two strips are located in the rear chest (112) and two others in the front chest (110). These strips are also found in the mattress.

The rear chest (112) (FIG. 7) is a fixed part, which permits the treatment of lower members. The control panel is installed on this part of the chest.

Therefore, the present invention includes a number of features, including the use of infrared rays distributed by radiants and radiating strips, a precise disposition and form of these strips within angles of the chest, specific conception by angles of the chest, a mattress including radiating strips, selected materials, a sliding system of the front chest for its opening, a bib type flap, an isolated air chamber, an electromagnetic security system, isolated wiring, a control panel placed on the exterior, a grill, for a capacity to rapidly obtain and conserve a target heat, a limited consumption of energy and therapeutically benefits connected to it.

Although the present invention has been described hereinabove by way of specific embodiments thereof, it can be modified, without departing from the spirit and nature of the subject invention as defined in the appended claims.

The invention claimed is:

1. A therapeutic apparatus, comprising:
   a base;
   a mattress supported by said base; and
   a cover, supported by said base over said mattress, said cover being elongate, with angles comprised between 30 and 60 degrees, said cover comprising a front part that slides relative to a rear part on rails, said cover being made of stainless steel and wood;
   wherein said mattress receives a user when said front part of said cover is slid rearward on said rails, said user lying on said mattress and then sliding said front part of said cover back towards the front of the rails over at least part of the user's body to be submitted to heat diffused by radiant strips, parts of the the user's body being able where the body is maintained uncovered and isolated from the rest of the body located under the cover by a removable flap mounted on the front part of said cover.

2. The therapeutic apparatus of claim 1, wherein said cover comprises an exterior surface made in stainless steel and an interior surface made in cedar wood, metallic braces between said exterior surface and said interior surface providing an air chamber.

3. The therapeutic apparatus of claim 1, wherein said front part comprises rollers.

4. The therapeutic apparatus of claim 1, wherein said removable flap is made in leather.

5. The therapeutic apparatus of claim 1, wherein said rear part is closed at a back end thereof by a panel of cedar wood.

6. The therapeutic apparatus of claim 1, wherein said radiant strips are mounted on internal walls of the cover and within said mattress.

7. The therapeutic apparatus of claim 1, wherein said radiant strips are formed of heating wires located within rubber layers.

8. The therapeutic apparatus of claim 1, comprising a rubberized silicone covered metal grill about the radiant strips.

9. The therapeutic apparatus of claim 1, further comprising an airtight case housing wiring.

10. The therapeutic apparatus of claim 1, further comprising a control panel, said control panel being mounted on said rear part.

11. The therapeutic apparatus of claim 10, wherein said control panel allows presetting temperature inside the apparatus.

12. The therapeutic apparatus of claim 1, wherein an air chamber is provided in said front and rear parts.

13. The therapeutic apparatus of claim 1, further comprising an electromagnetic security system.

14. The therapeutic apparatus of claim 1, wherein said base comprises cedar wood.

15. The therapeutic apparatus of claim 1, wherein said mattress comprises leather on an outside thereof, and radiating strips inserted between two layers of felt on an inside thereof.

* * * * *